(12) United States Patent
Laemle et al.

(10) Patent No.: US 10,414,204 B2
(45) Date of Patent: *Sep. 17, 2019

(54) WRITING IMPLEMENT WITH BEARING COUPLED ROTARY DEVICE

(71) Applicants: David A. Laemle, Westwood, NJ (US); Marc Puglisi, Wayne, NJ (US)

(72) Inventors: David A. Laemle, Westwood, NJ (US); Marc Puglisi, Wayne, NJ (US)

(73) Assignees: Davro Design, LLC, Westwood, NJ (US); Prostock, LLC, Wayne, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/957,175

(22) Filed: Apr. 19, 2018

(65) Prior Publication Data
US 2018/0290483 A1 Oct. 11, 2018

Related U.S. Application Data

(63) Continuation of application No. 15/622,889, filed on Jun. 14, 2017, now Pat. No. 9,950,556.
(Continued)

(51) Int. Cl.
*B43K 29/00* (2006.01)
*A61M 21/02* (2006.01)
(Continued)

(52) U.S. Cl.
CPC ............. *B43K 29/00* (2013.01); *A61M 21/02* (2013.01); *A63H 1/00* (2013.01); *B43K 23/04* (2013.01);
(Continued)

(58) Field of Classification Search
CPC .... B43K 29/00; B43K 29/002; B43K 29/004; B43K 29/007; B43K 29/08; B43K 29/087;
(Continued)

(56) References Cited

U.S. PATENT DOCUMENTS

| | | |
|---|---|---|
| 3,811,218 A | 5/1974 | Salmon et al. |
| 5,086,577 A | 2/1992 | Abernethy |

(Continued)

FOREIGN PATENT DOCUMENTS

| | | |
|---|---|---|
| CN | 102909999 A | 2/2013 |
| DE | 29921794 U1 | 3/2000 |

OTHER PUBLICATIONS

Advertising Literature—Ballpoint Pen Fan—https://www.yoycart.com/Product/549129697737/- © 2009-2013 Yoycart.com All rights reserved. 1 page brochure.
(Continued)

*Primary Examiner* — David J Walczak
(74) *Attorney, Agent, or Firm* — St. Onge Steward Johnston & Reens, LLC

(57) ABSTRACT

A writing instrument that includes an elongated body with a first end and a second end, wherein the first end is coupled to a post and the second end has an aperture for a writing tip to be exposed, a rotary bearing coupled to the post, wherein the rotary bearing has a central opening and wherein the post at least partially extends through the central opening of the rotary bearing, and a rotary device coupled to the bearing.

20 Claims, 18 Drawing Sheets

Related U.S. Application Data

(60) Provisional application No. 62/481,810, filed on Apr. 5, 2017.

(51) Int. Cl.
 *A63H 33/00* (2006.01)
 *A61M 21/00* (2006.01)
 *A63H 1/00* (2019.01)
 *B43K 23/04* (2006.01)
 *B43K 23/08* (2006.01)
 *B43K 25/02* (2006.01)

(52) U.S. Cl.
 CPC ............ *B43K 23/08* (2013.01); *B43K 25/026* (2013.01); *A61M 2021/0022* (2013.01); *A61M 2021/0027* (2013.01); *A63H 33/00* (2013.01)

(58) Field of Classification Search
 CPC .......... B43K 29/10; B43K 9/12; B43K 29/18; A61M 21/02; A61M 2021/0022; A63H 33/00
 See application file for complete search history.

(56) References Cited

U.S. PATENT DOCUMENTS

| | | |
|---|---|---|
| 6,270,021 B1 | 8/2001 | Bolton |
| D482,064 S | 11/2003 | Steiner et al. |
| 7,179,004 B2 * | 2/2007 | Cetera ................ B43K 25/026 |
| | | 24/11 HC |
| 9,211,757 B2 | 12/2015 | Osborne |
| 2007/0195529 A1 | 8/2007 | Yu |
| 2011/0027002 A1 | 2/2011 | Castro et al. |
| 2011/0103877 A1 | 5/2011 | Liu |

OTHER PUBLICATIONS

Advertising Literature: Ballpoint pen fashion pen with a fan pen—Manufactured by: Shibell, Source: https://www.alibaba.com/productdetail/Shibell-top-quality-ballpoint-penfashion_60194950875.html?s=p, The publication date of the article (as shown by google) is Jun. 20, 2016. 1 page.

Advertising Literature: Twist Action Ballpoint Pen with Snap on Fan—https://www.imprintitems.com/blog/20561/twistaction-ballpoint-pen-with-snap-on-fan/, Date The publication date of the article (as shown by google) is Feb. 3, 2015. 1 page.

* cited by examiner

WRITING IMPLEMENT WITH BEARING COUPLED ROTARY DEVICE

FIELD OF THE INVENTION

The present invention relates to a rotary device which is affixed to a writing implement, such as a pen or other marking device, using a rotary bearing, such as a bearing having a plurality of rolling elements within a bearing case.

BACKGROUND OF THE INVENTION

Rotating sensory devices also known as fidget toys or gadget toys, are self-regulation tools to help with focus, attention, calming, and active listening. More particularly, Fidgets and Gadgets are devices that provide the sensory input that many children and adults with special needs such as autism and Attention Deficit Hyperactivity Disorder (ADHD) to help them mitigate symptoms of such disorders. Whether it is visual or tactile, the self-regulation rotary devices have the power to capture an individual's attention, making the sensory device a powerful reinforcer in applied behavioral analysis programs.

For educators and therapists, it is easy to point out a restless individual. The individual who is always restless in his/her seat, the individual who is always getting up to use the bathroom, the individual who is constantly tapping his/her foot, rummaging through things on their desk, or picking at a name tag. Individuals with these forms of special needs hinder their own learning and productivity because of their short attention spans. This nervousness and excess energy can and often does continue for a lifetime.

Research has confirmed the importance of movement and sensory input while learning and working, and focus is enhanced when sensory input devices are introduced. Students and adults with a medical diagnosis of ADHD showed significant improvement academically and in the work environment. What is needed is a device that will incorporate the benefits of the sensory input device with a means of communication and expression.

SUMMARY OF THE INVENTION

Accordingly, it is an object of the present invention to provide a writing implement that also provides stimulation and sensory input.

Still other objects and advantages of the invention will in part be obvious and will in part be apparent from the specification.

In order to overcome the deficiencies of the prior art and to achieve at least some of the objects and advantages listed, the invention comprises a writing instrument, including an elongated body with a first end and a second end, wherein the first end is coupled to a post and the second end has an aperture for a writing tip to be exposed, a rotary bearing coupled to the post, wherein the rotary bearing has a central opening and wherein the post at least partially extends through the central opening of the rotary bearing, and a rotary device coupled to the bearing.

In some embodiments, the rotary device is powered by a non-electric power.

In certain embodiments, the rotary bearing includes an inner race and an outer race and a plurality of rolling elements positioned between the inner race and the outer race.

In some cases, the post is a plunger that actuates the writing tip of the writing instrument.

In certain embodiments, the rotary device is a rotary sensory device.

In some embodiments, the post includes a plurality of external threads, wherein the rotary bearing is coupled to the post via a screw cap such that the rotary bearing is positioned between the first end of the writing instrument and the screw cap, and wherein the screw cap includes a plurality of threads inside of the screw cap that interact with the plurality of external threads on the post. In certain of these embodiments, the writing instrument further includes a support member having a base plate with a central opening and a hollow cylindrical body extending from the base plate, wherein the post is extended through the central opening and the hollow cylindrical body of the support member, and wherein the rotary bearing is supported between the base plate and the screw cap.

A writing instrument is also provided having an elongated body with a first end and a second end, a rotary bearing coupled to the elongated body, and a rotary device coupled to the bearing, wherein the rotary device is not electrically powered.

In certain embodiment, the rotary device is actuated by manually exerting a rotational force on the rotary device.

A writing instrument is further provided, including an elongated body with a first end and a second end, a rotary bearing coupled to the elongated body, wherein the bearing has an inner race and an outer race and a plurality of rolling elements positioned between the inner race and the outer race, and a rotary device coupled to the bearing.

In some embodiments, the rotary bearing is coupled to the first end of the elongated body.

In certain embodiments, the second end of the elongated body has an aperture through which a writing implement is exposed.

In some embodiments, the rotary device is a rotary sensory device. In additional embodiments, the rotary device has a plurality of wings. In further embodiments, the rotary device is an object. In yet further embodiments, the rotary device is a wheel.

In certain embodiments, the writing instrument is a pen.

In some cases, the rotary device is not electrically powered.

In certain embodiments, the rolling elements are balls.

In some embodiments, the rotary bearing is coupled to the elongated body via an adhesive. In additional embodiments, the rotary bearing is coupled to the elongated body via friction between the inner race of the rotary bearing and the elongated body.

In certain embodiments, the writing instrument further includes a coupling member that couples the bearing to the elongated body. In some of these embodiments, the rotary device has a plane of rotation and the coupling member is adjustable such that the plane of rotation of the rotary device is altered. In additional embodiments, the rotary device is configured to rotate while resting on a flat surface and wherein the coupling member is configured to accommodate at least one of the first end and the second end of the writing instrument inserted therein such that the writing instrument is maintained in an upright position.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

DETAILED DESCRIPTION OF THE INVENTION

Figure 1:
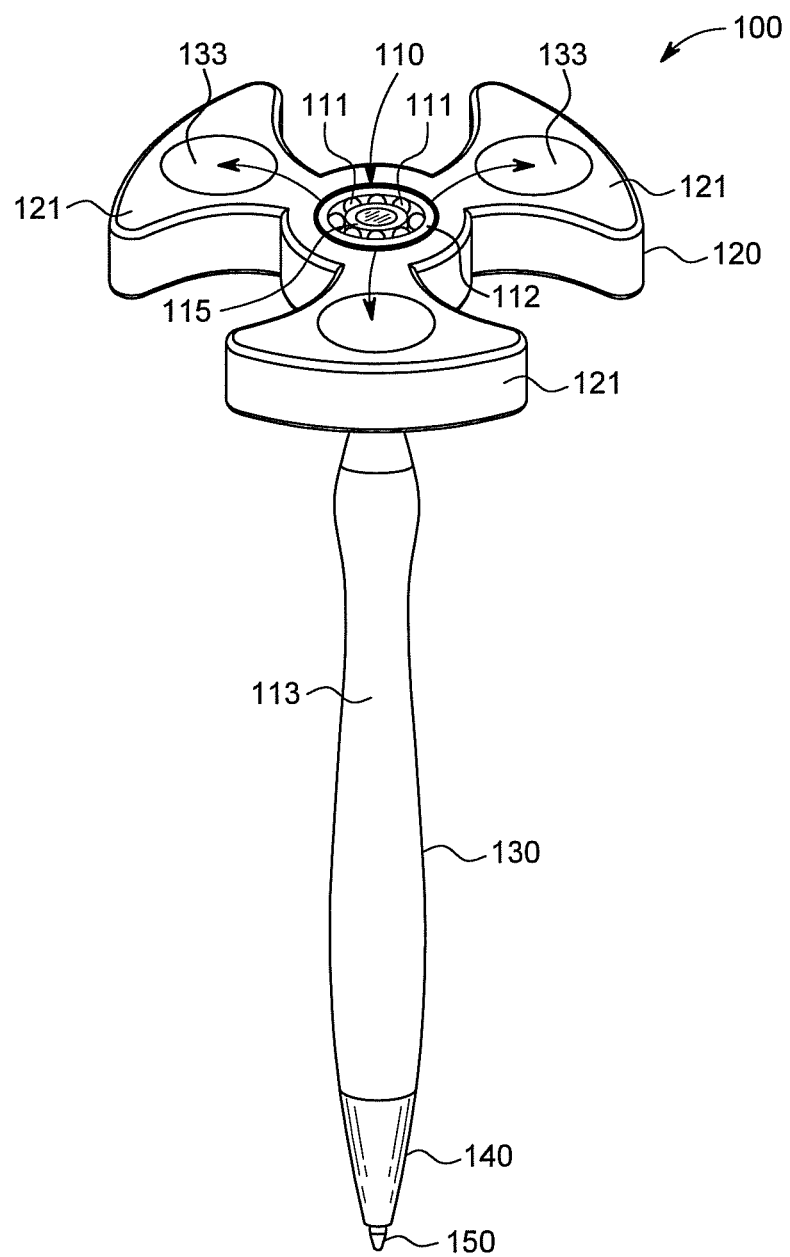
FIG. 1 is a top perspective view of a writing implement with a bearing coupled rotary device according to an embodiment of the present invention.

The basic components of an exemplary embodiment of a writing implement 100 with a bearing coupled rotary device in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

Figure 2A:
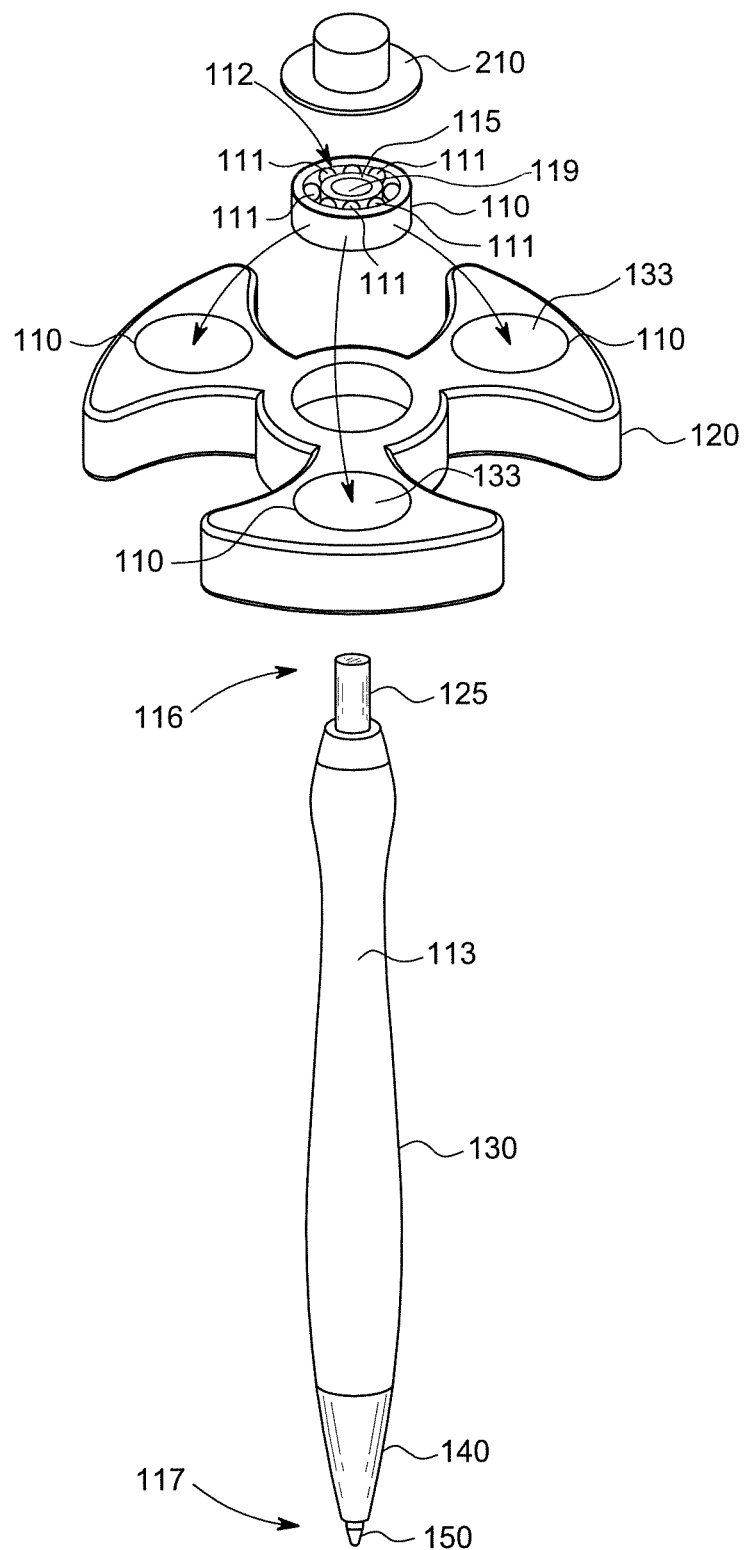
FIG. 2A is an exploded view of the writing implement with the bearing coupled rotary device of FIG. 1.

FIG. 1 shows a rotary device 120 coupled to a writing implement 130 using bearing 112. It is contemplated that the present invention encompasses any type of a writing implement, such as, for example, a pen shown in FIG. 1, or a pencil shown in FIGS. 12 and 14A and 14B, or a stylus. The writing implement has an elongated body or a barrel 113 with first end 116 and a second end 117, as illustrated in FIG. 2A. The second end has an aperture 140 through which a writing tip 150 is extended. In the case of a pencil or a stylus, the writing or marking tip is positioned at the second end. The first end 116 may contain an actuation mechanism for the writing instrument, an eraser, or another feature of the writing instrument.

Any kind of a rotary bearing may be used in accordance with the present invention to couple the rotary device 120 to the writing implement 130. In the embodiment shown in FIGS. 1 and 2, the bearing 112 includes an outer race 110 and inner race 115 positioned within the outer race. The bearing 112 also has a central opening 119. A groove created between the inner race 115 and the outer race 110 contains a plurality of rolling elements 111, shown in FIG. 1 as balls. The rolling elements 111 are loosely fitted within the groove of inner race 115 and the outer race 110 such that they can freely move within the groove, thereby enabling a rotational movement of the outer race 110 with respect to the inner race 115.

Figure 12:
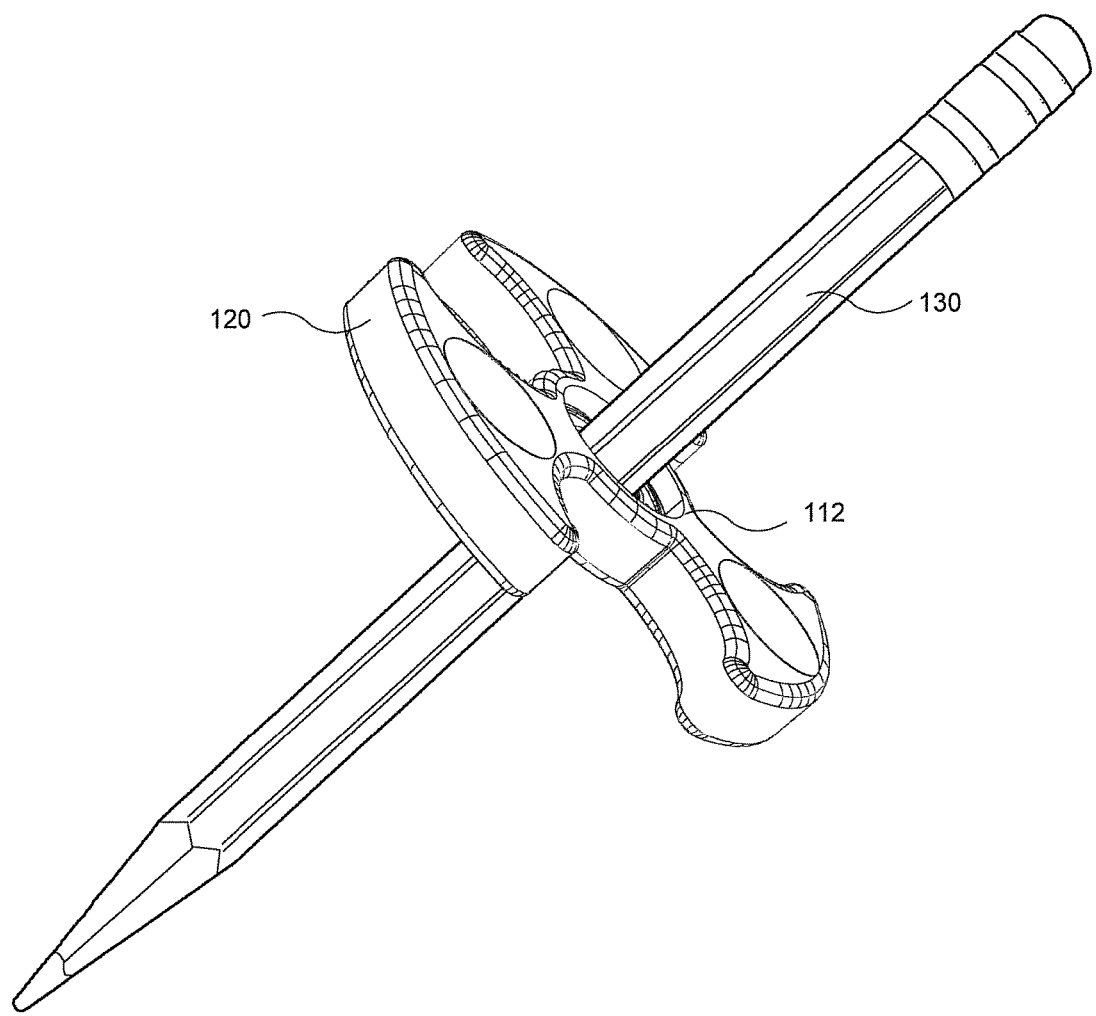
FIG. 12 is a side perspective view of an embodiment of the writing instrument with a bearing coupled rotary sensory device in accordance with the invention.

The size of the bearing 112 and an inner diameter of the central opening 119 in the bearing may vary depending on a desired application. For example, in some embodiments, the diameter of the central opening 119 is large enough to accommodate the elongated body of the writing implement 130 inserted therethrough, as illustrated in FIG. 12. In other embodiments, the diameter of the central opening 119 of the bearing 112 may be smaller to accommodate a post 125 extending from the writing implement, as shown in FIG. 2A. Different types of the rotary bearings may be used to adjust for the rotary device's spin time, vibration, and noise, leading to unique sensory feedback.

The bearing 112 is coupled to the writing instrument 130 by any suitable mechanism. In the embodiment shown in FIG. 12, the inner race of the bearing 112 is in direct contact with the body of the writing instrument 130, which is inserted through the central opening in the bearing 112. The inner race may affixed to the writing instrument body via an adhesive, or friction between the inner race and the writing instrument body 130, or via other suitable mechanism.

Figure 2B:
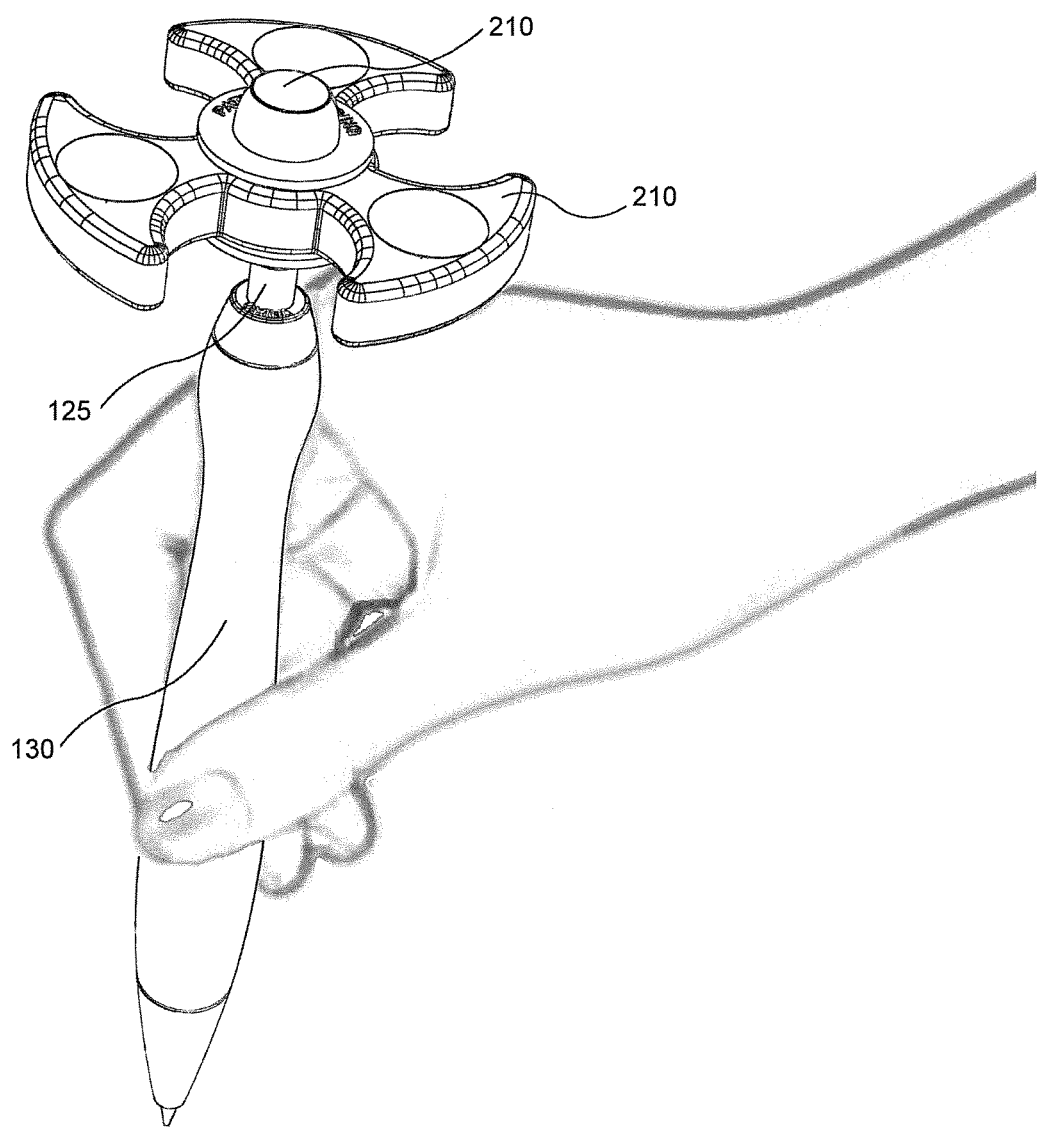
FIG. 2B illustrates the writing implement of FIG. 2A being used as a writing device.

In the embodiment shown in FIGS. 2A and 2B, the inner race 115 of the bearing is in direct contact with the post 125 placed at the first end 116 of the pen 130 and at least partially extending through the central opening 119 in the bearing 112. Similarly to the embodiment shown in FIG. 12, the inner race 115 is affixed to the post 125 via an adhesive, or friction between the inner race and the post, or via other suitable mechanism. The post 125 may be a plunger used to actuate the writing tip 150 of the pen 130. In other embodiments, the post is used just for the purpose of affixing the bearing and the rotary device to the pen. It is understood that the writing device 130 may be actuated by any other suitable mechanism, such as a twist action or a sliding actuator positioned in a slit in the pen body.

As shown in the exploded view of FIG. 2A, the rotary device 120 is positioned over the post 125 of the pen 130. The bearing 112 is coupled to the central opening in the rotary device such that the outer race 110 of the bearing fits snugly inside the rotary device opening. The post 125 extends through the central opening 119 in the inner race 115 of the bearing. A cap 210 may also be positioned over the portion of the post 125 that extends out of the top of the bearing to further affix the bearing 112 and the rotary device 120 to the pen 130. The cap may be either press fit onto the post or may have internal threads that interact with external threads provided on the post. The rolling elements 111 positioned in the groove between the inner race 115 and the outer race 110 of the bearing assist in the rotational motion of the rotary device 120.

Figure 4:
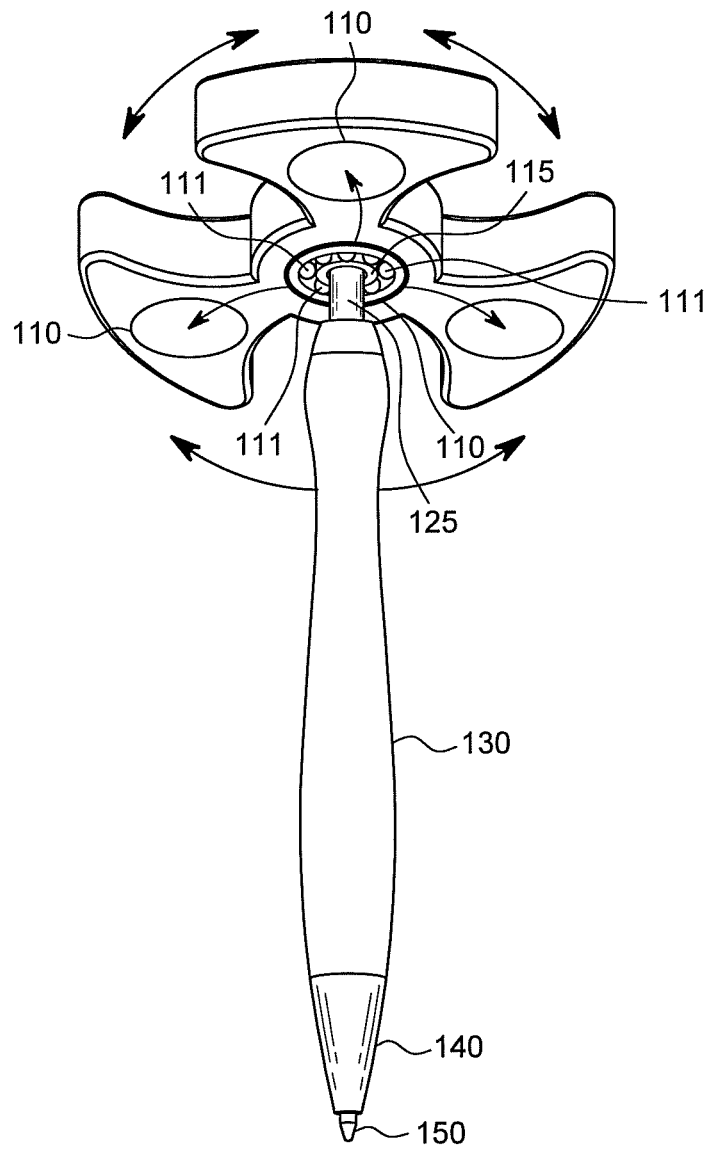
FIG. 4 is a bottom perspective view of the writing implement with the bearing coupled rotary device of FIG. 1.

When in use, a person exerts rotation force on one side of the rotary device 120 in either clockwise or counterclockwise direction, as shown in FIG. 4, thereby causing the rotary outer race 110 with the affixed rotary device 120 to rotate around its axis. During the rotation, the inner race 115 of the bearing remains stationary and affixed to the writing instrument 130. The use of the rotary bearing allows the rotary device 120 to spin for a prolonged period of time after manual actuation without being electrically powered.

The rotary device 120 is actuated while the writing instrument 130 is held in a person's one hand. The rotary device spins regardless of whether the writing instrument is held upright or titled or upside down. Alternatively, the writing instrument may be turned upside down and the top of the rotary device 120 with the bearing is placed on a flat surface such that the writing instrument is balanced in the upright position. Then, the rotary device 120 is actuated manually and it spins while the pen 130 rests on the flat surface in the upright position without the need for the person to hold it. When the rotary device is not in use, the writing instrument 130 may be used as a regular writing device, as shown in FIG. 2B.

Figure 3:
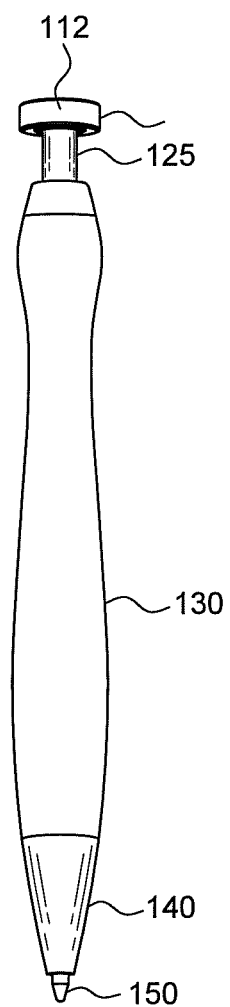
FIG. 3 is a front perspective view of the writing implement of FIG. 1, showing with the bearing but without the rotary device.
Figure 5:
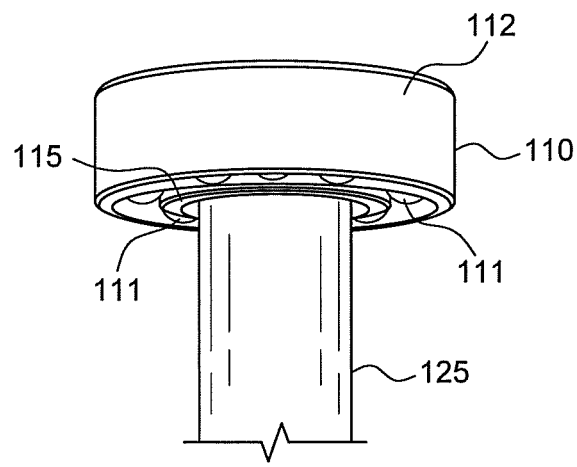
FIG. 5 is an enlarged front perspective view of the bearing of FIG. 1 coupled to a post.
Figure 6:
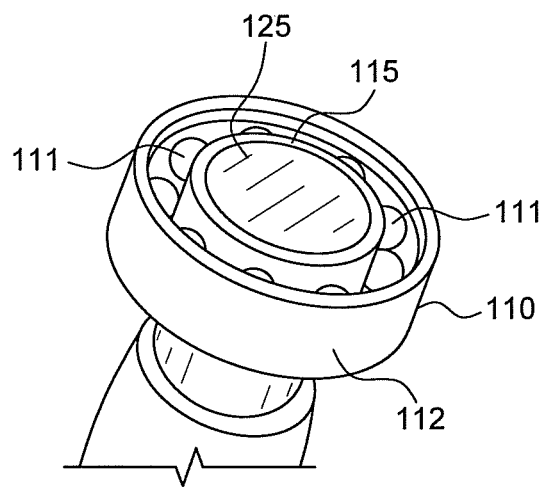
FIG. 6 is an enlarged angled top view of the bearing coupled to the post of FIG. 5.

FIG. 3 shows the embodiment of FIG. 1 without the rotary device. The bearing 112 is placed over the post 125 of the writing instrument 130. FIGS. 5 and 6 are enlarged views of the post 125 with the affixed bearing 112. In this embodiment, the top portion of the post 125 is flush with the top portion of the bearing 112 for aesthetic reasons. It is understood that in other embodiments, such as shown in FIGS. 15A-15B, the top portion of the post 125 may extend above the top of the bearing 112 to engage a screw cap.

In further embodiments, the bearing 112 is coupled to the writing instrument 130 via a coupling member, such as a screw cap, a ring locking clip, or any other suitable coupling mechanism a writing implement to a bearing.

Figures 14A, 14B:
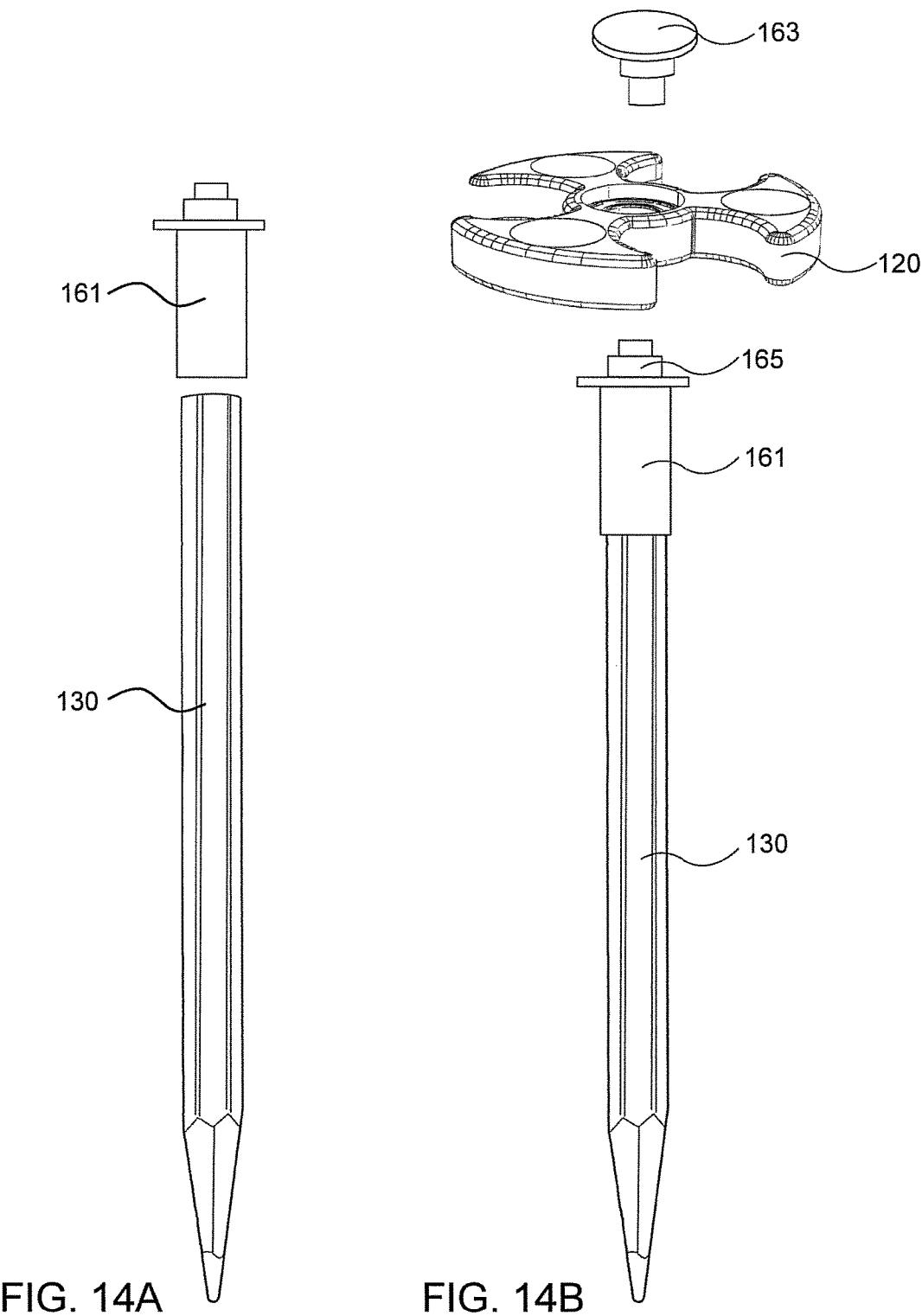
FIGS. 14A and 14B are exploded views of the writing instrument with the bearing coupled rotary device in accordance with the invention, showing a coupling member that affixes the bearing to the writing instrument.

One exemplary embodiment of the coupling member is illustrated in FIGS. 14A and 14B. The coupling member 161 has a generally cylindrical body with an inner diameter that is chosen so that the body fits tightly over the elongated body of the writing instrument 130, in this case a pencil. The tip portion of the coupling member 161 has a protrusion 165 sized and shaped to fit inside the central opening of the bearing, which is affixed to the rotary device 120. When in use, the coupling member 161 is positioned on the writing instrument 130 and the bearing 112 with the rotary device 120 is affixed to the top part of the coupling member 161 via the protrusion 165. A cap 163 may be optionally placed over the top portion of the bearing 112 and snapped into or screwed onto the protrusion 165 to more securely attach the rotary device to the writing instrument.

Figure 15A:
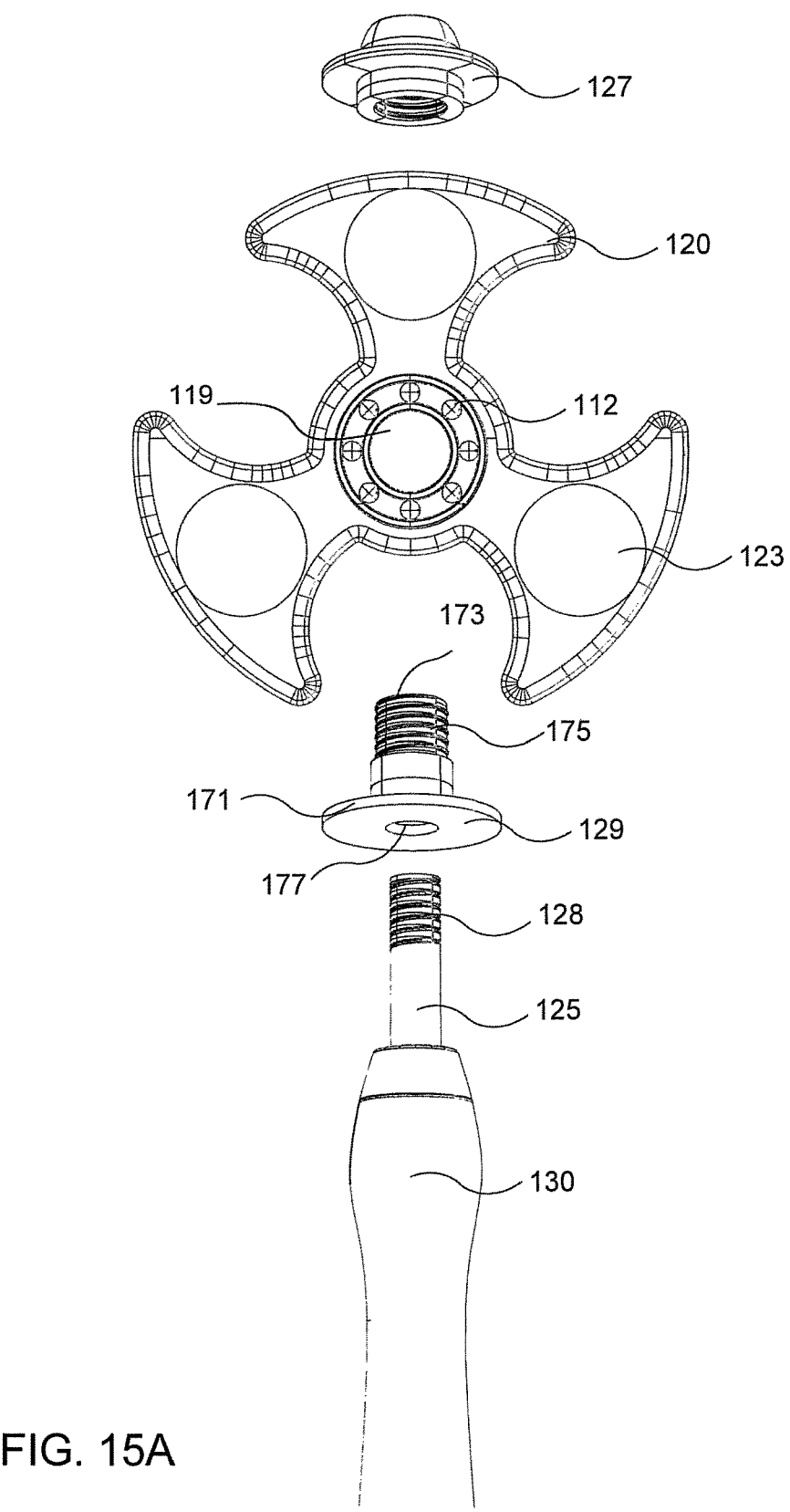
FIG. 15A is an exploded front view of the writing instrument with the bearing coupled rotary device, showing another embodiment of the coupling member.
Figure 15B:
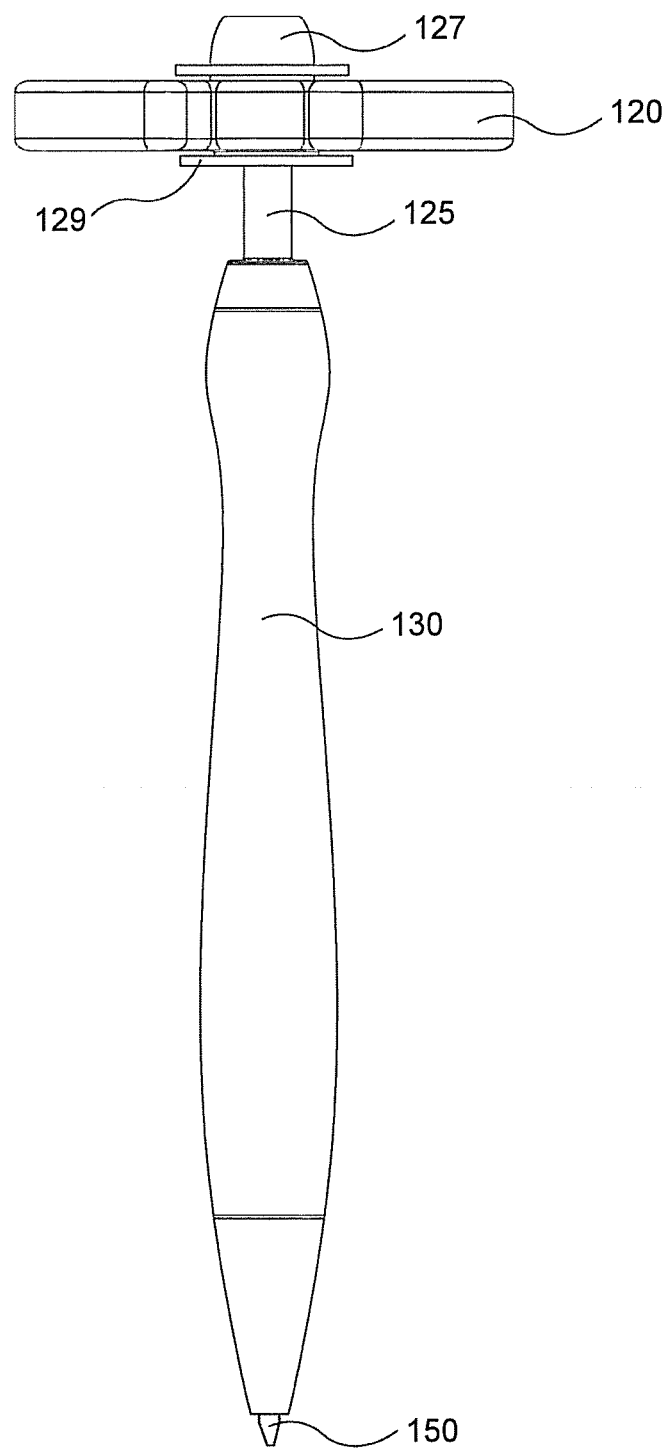
FIG. 15B is a front view of the writing instrument with the bearing coupled rotary device of FIG. 15A, shown in assembled configuration.

FIGS. 15A and 15B illustrate another exemplary embodiment of the coupling member. In this embodiment, the writing instrument 130 has a post 125 at its first end, which may also act as the actuation mechanism for the writing tip 150. The post 125 includes a plurality of external threads 128 at its upper portion. A support member 129 having a base plate 171 with a central opening 177 and a hollow cylindrical body 173 extending from the base plate is placed over the post 125. The hollow body 173 of the support member 129 has a plurality of internal threads (not shown) that interact with the plurality of external threads 128 on the post 125 such that the support member is affixed to the post. It is also contemplated that the support member may be press fit over the post and affixed to it by friction between the two.

Next, the bearing 112 with the coupled rotary device 120 is placed over the cylindrical body 173 of the support member 129 via the central opening 119. The top portion of the cylindrical body 173 of the support member 129 that extends above the bearing has external threads 175 that interact with the internal threads of the screw cap 127 to further affix the bearing and the rotary device to the post. The support member 129 also functions to support the rotating rotary device 120 such that it does not slip down the post 125 and/or the pen body, as shown in FIG. 15B.

Figure 16:
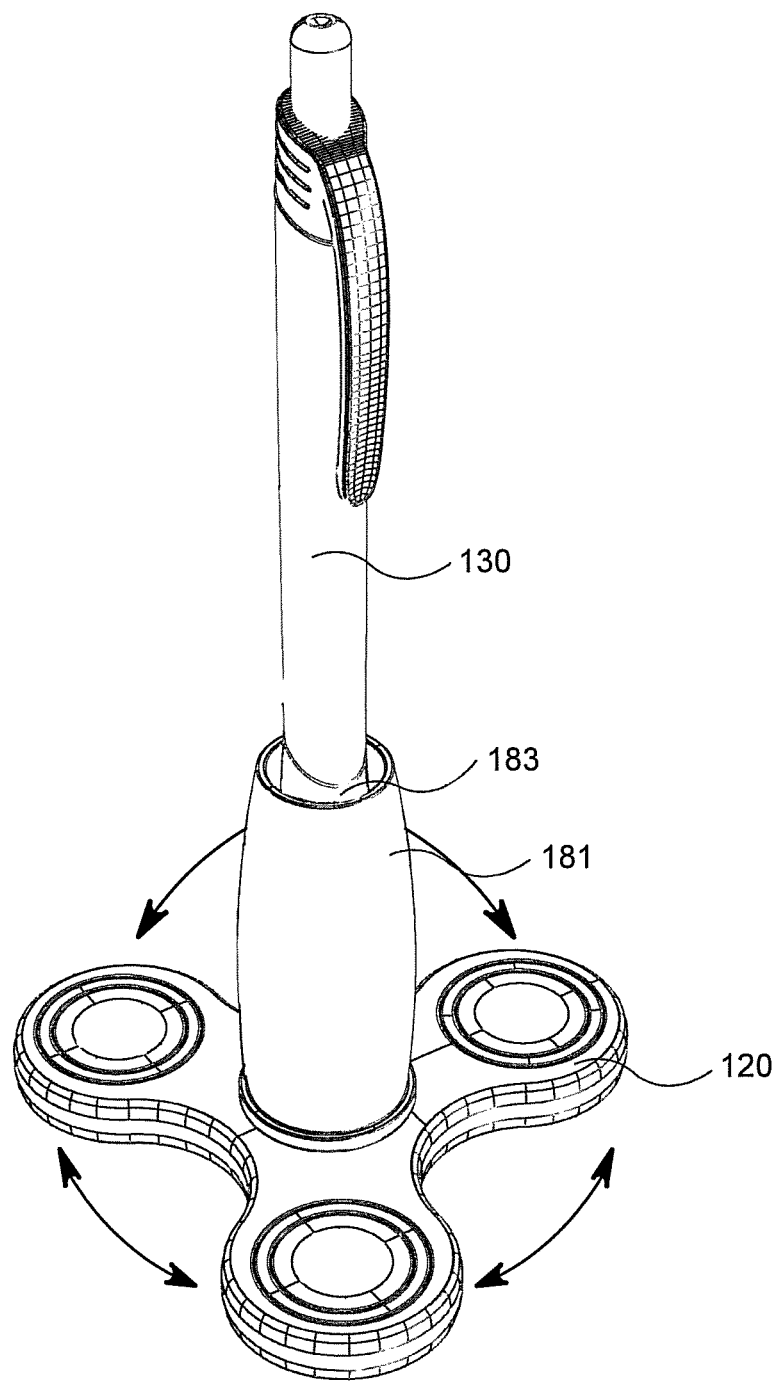
FIG. 16 is a front perspective view of the writing instrument with the bearing coupled rotary device, showing an additional embodiment of the coupling member.

A further embodiment of the coupling member is illustrated in FIG. 16. In this embodiment, the coupling member 181 has an elongated hollow body with an opening 183 at the top. The bottom end of the coupling member 181 is coupled to the bearing (not shown) and the rotary device 120 such that the rotary device is capable of spinning while being connected to the coupling member 181. The coupling member 181 is affixed to the bearing by any suitable mechanism. For example, the bottom portion of the coupling member 181 may have a protrusion (not shown) that extends through the central opening in the bearing. A bottom cap may also be fitted onto the bottom of the protrusion to more securely affix the bearing and the rotary device to the coupling member. The bottom of the cap is preferably flat such that the rotary device 120 with the coupling member 181 can stably rest on a flat surface.

The hollow interior of the coupling member 181 is shaped to accommodate at least one of the first end and the second end of the writing instrument 130 inserted therein such that the writing instrument is maintained in an upright position. In the embodiment shown in FIG. 16, a writing tip end of the pen 130 is inserted into the hollow body of the coupling member 181 through the opening 183. This way the coupling member 181 also functions as a writing instrument stand. The rotary device 120 is configured to rotate while resting on a flat surface with the coupling member supporting the writing instrument 130 in an upright position. It is noted that in this embodiment of the coupling member, the pen 130 can also be held by a person with the coupling member and the rotary device positioned on the pen, and the rotary device can be manually actuated to spin while the pen is being held.

Figure 17A:
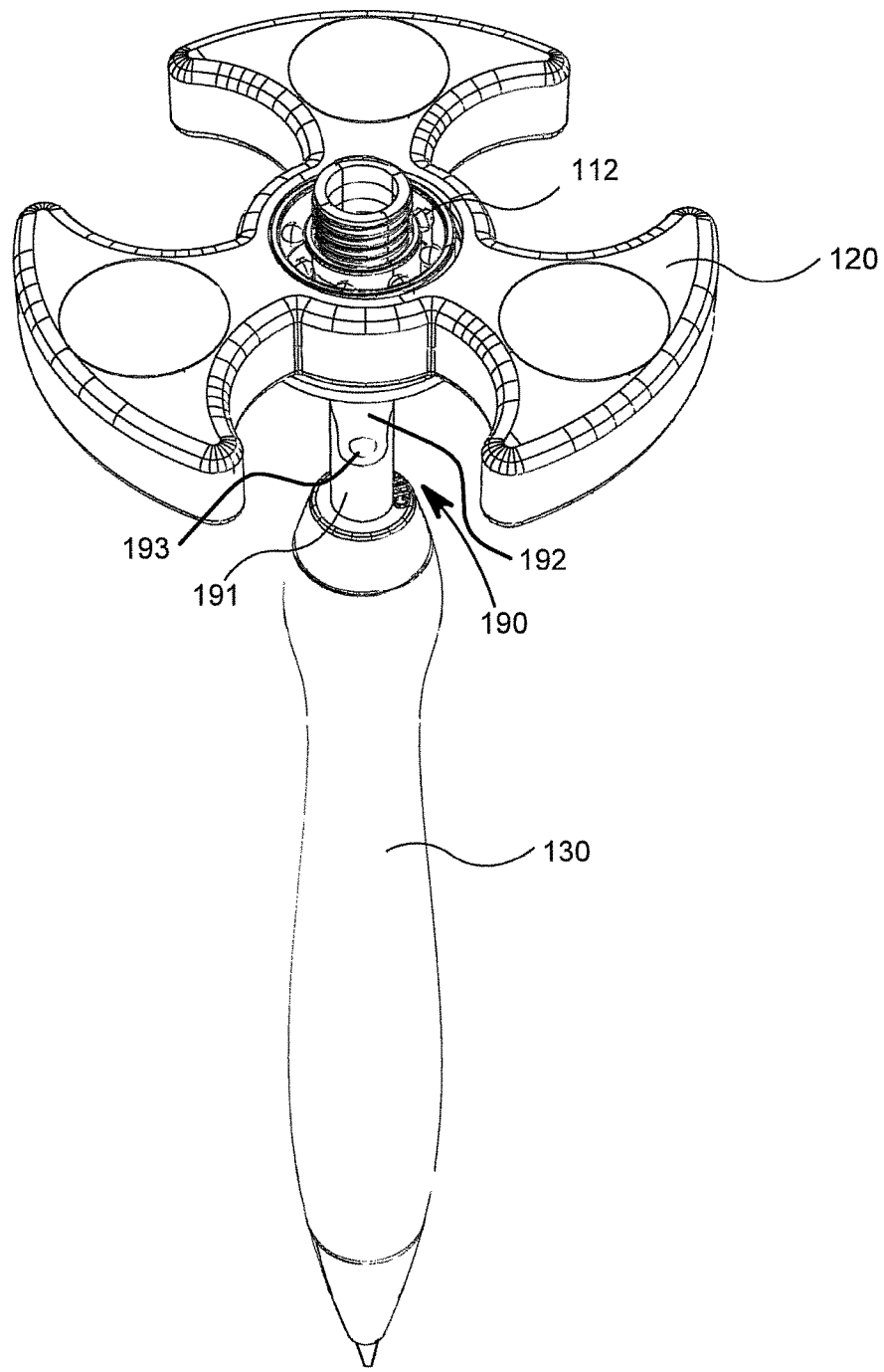
FIGS. 17A and 17B are front perspective views of the writing instrument with the bearing coupled rotary device, showing another exemplary embodiment of the coupling member.
Figure 17B:
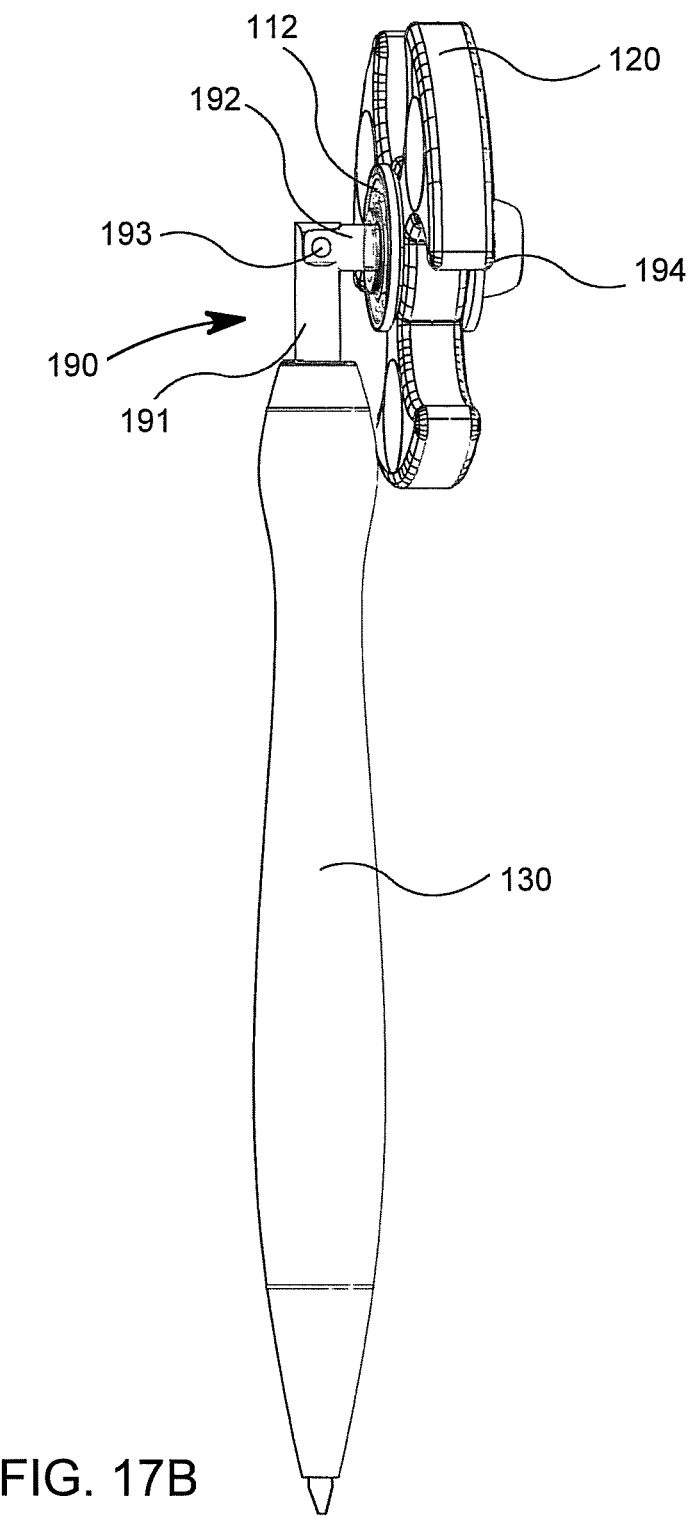

FIGS. 17A and 17B illustrate an additional embodiment of the coupling member. In this embodiment, the coupling member 190 includes a bottom part 191 coupled to one end of the writing instrument 130 and a second part 192. The first and second parts of the coupling member are connected via a hinge 193 that allows the second part 192 to move with respect to the first part 191. The bearing 112 with the coupled rotary device 120 is placed over the top of the second part 192 and is affixed thereto by any suitable means, such as, for example, a cap shown in FIG. 17B.

When in use, the coupling member 190 may be maintained in the straight position shown in FIG. 17A while the rotary device 120 is spinning. Alternatively, the second part 192 of the coupling member may be tilted to any desired angle about the hinge 193 to alter the plane of rotation of the rotary device 120, as shown in FIG. 17B.

Any desired object may be used as the rotary device in accordance with the present invention. In one advantageous embodiment shown in FIGS. 1 and 2A, the rotary device 120 is a sensory device. Rotary sensory devices have been known to relieve stress and help people who have trouble with focusing or fidgeting, such as those with ADHD, autism or anxiety. The rotary sensory device 120 includes three prongs or wings 121 positioned around a central opening, into which the rotary bearing 112 is placed. The rotary device 120 may be made with any suitable material, such as metal or plastic.

Figure 7:
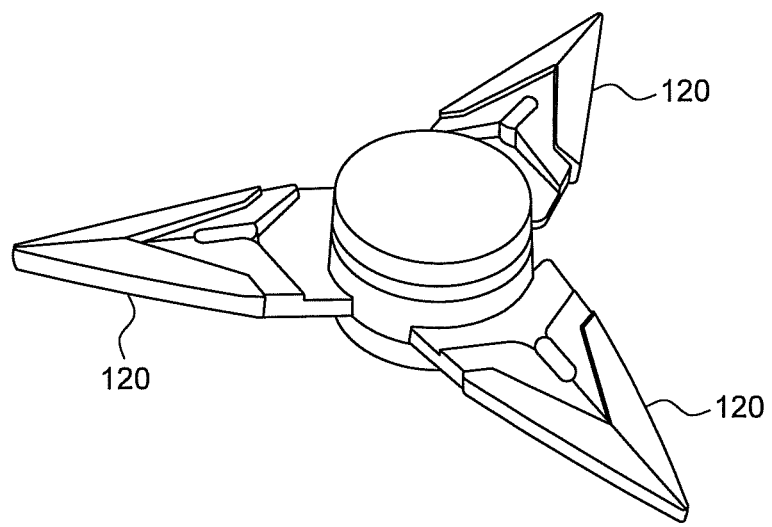
FIG. 7 is a top perspective view of an embodiment of the rotary sensory device.
Figure 8:
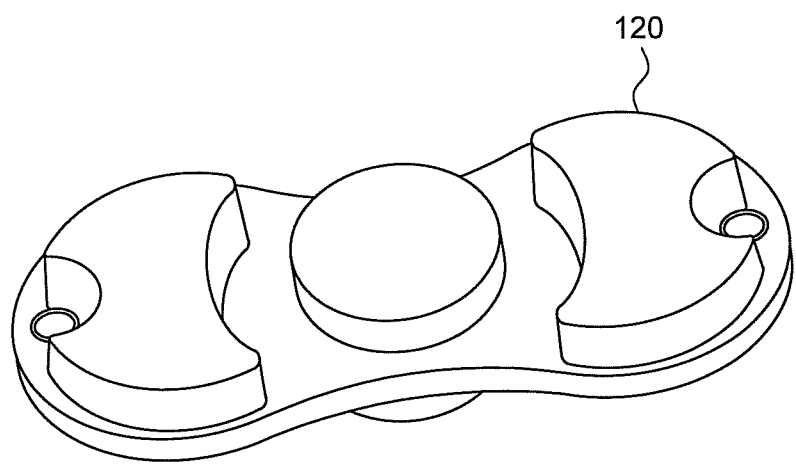
FIG. 8 is a top perspective view of another embodiment of the rotary sensory device.
Figure 9:
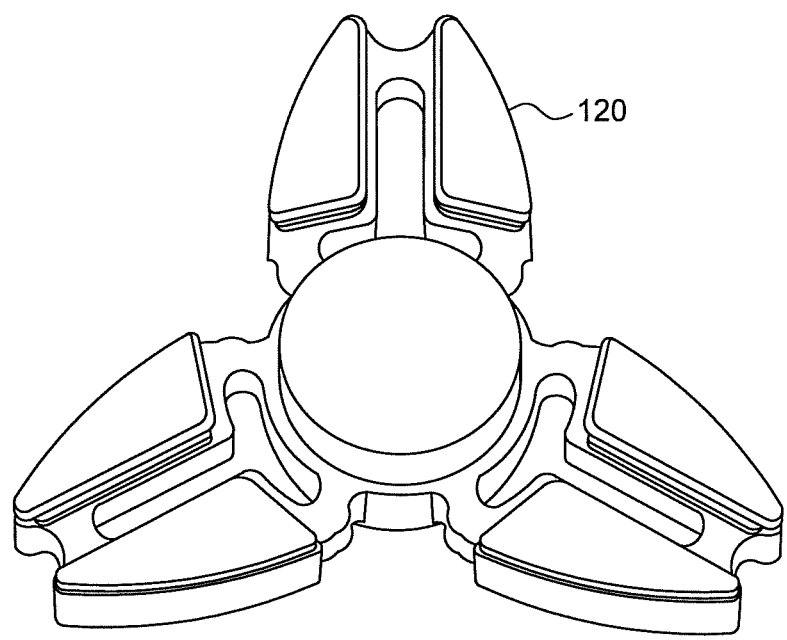
FIG. 9 is a top perspective view of an additional embodiment of the rotary sensory device.

It is understood that the sensory rotary device 120 may have two prongs, as shown in FIG. 8, or more than three prongs. The prongs may be of any desired shape and design and preferably have an aerodynamic design to facilitate longer spin time. Some exemplary embodiments of the sensory rotary devices are illustrated in FIGS. 7-9. In some embodiments, the prongs 121 of the rotary device include one or more weighted members 123, such as metal pieces, that assist in balancing of the rotary device and thus enabling a longer spin time, as illustrated in FIG. 15A. In additional embodiments, a light source such as an LED may be placed in the prongs 121 of the rotary device 120. The light source may be motion activated such that it turns on when the rotary device 120 begins to spin.

In an additional embodiment shown in FIG. 1, one or more of the prongs 121 may include an opening 133 sized such that it can receive the rotary bearing 112. In this case, the bearing may be placed in the central opening in the rotary device 120 or in any of the openings 133 in the prongs 121, thus creating more design variants.

Figure 10:
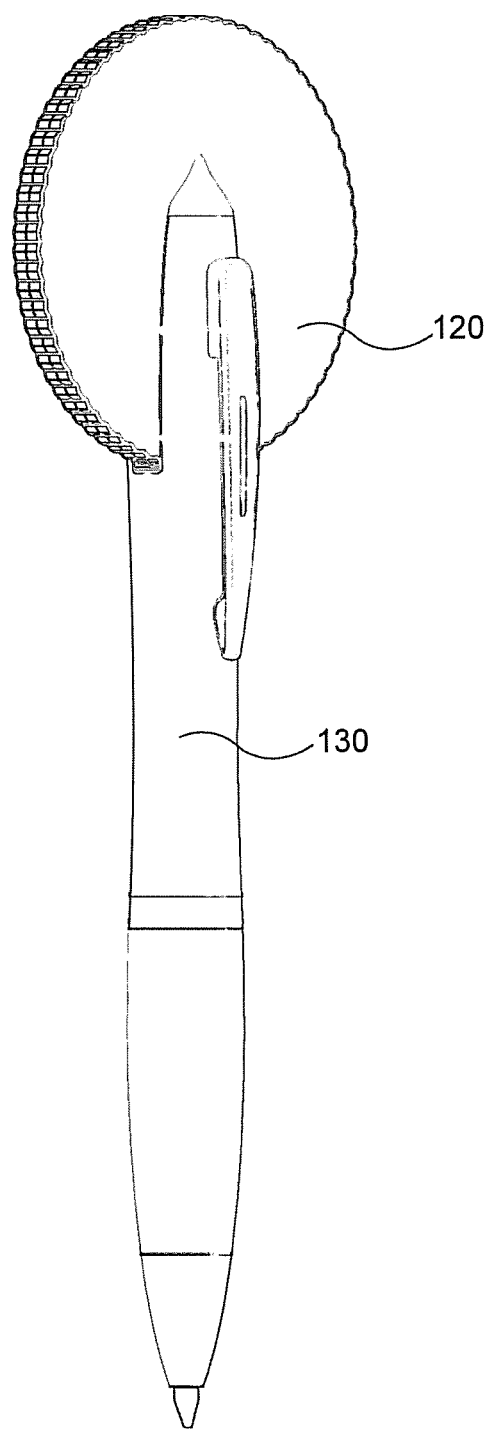
FIG. 10 is a front view of the writing instrument with another exemplary embodiment of the rotary device.

Other types of rotary devices having various shapes and designs may be used in accordance with the present invention. For example, as shown in FIG. 10, the rotary device may be a wheel 120 that spins in a vertical plane of rotation. In this embodiment, the wheel is coupled to a rotary bearing (not shown), which in turn is coupled to the top portion of the writing instrument 130. The writing instrument 130 has a vertical slit in its top portion that accommodates the bearing and the wheel 120. The slit is wide enough to allow the wheel 120 to freely rotate therein. It is understood that the wheel may also spin in a horizontal plane of rotation, similar to the rotary device of FIGS. 1 and 2, or in any other plane of rotation.

Figure 11:
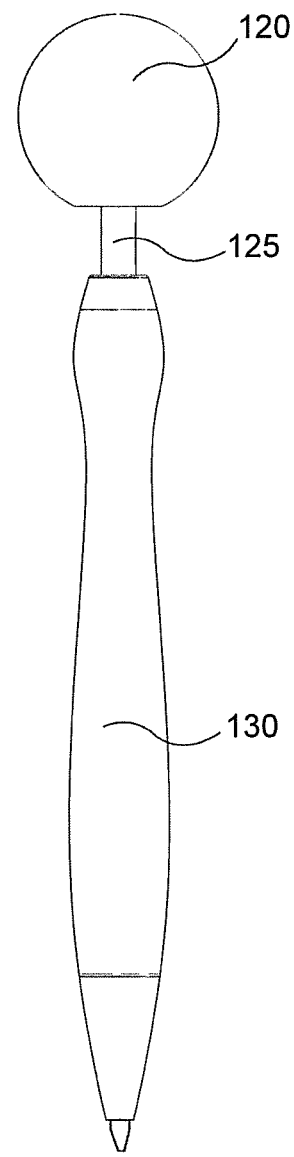
FIG. 11 is a front view of the writing instrument with an additional exemplary embodiment of the rotary device.

FIG. 11 illustrates another embodiment of the rotary device 120, which is in a shape of a ball. In this embodiment, the rotary bearing in placed in a central opening inside the ball 120 and the pen post 125 is inserted therethrough to couple the rotary device 120 to the pen 130. It is understood that the rotary device may have any other desired shape. The rotary device 130 may also have any desired indicia printed on its surface by any suitable method, as shown in FIGS. 10 and 11. For example, it may be desirable to print a promotion image on the rotary device such that the writing instrument may be used for promotional purposes.

Figure 13:
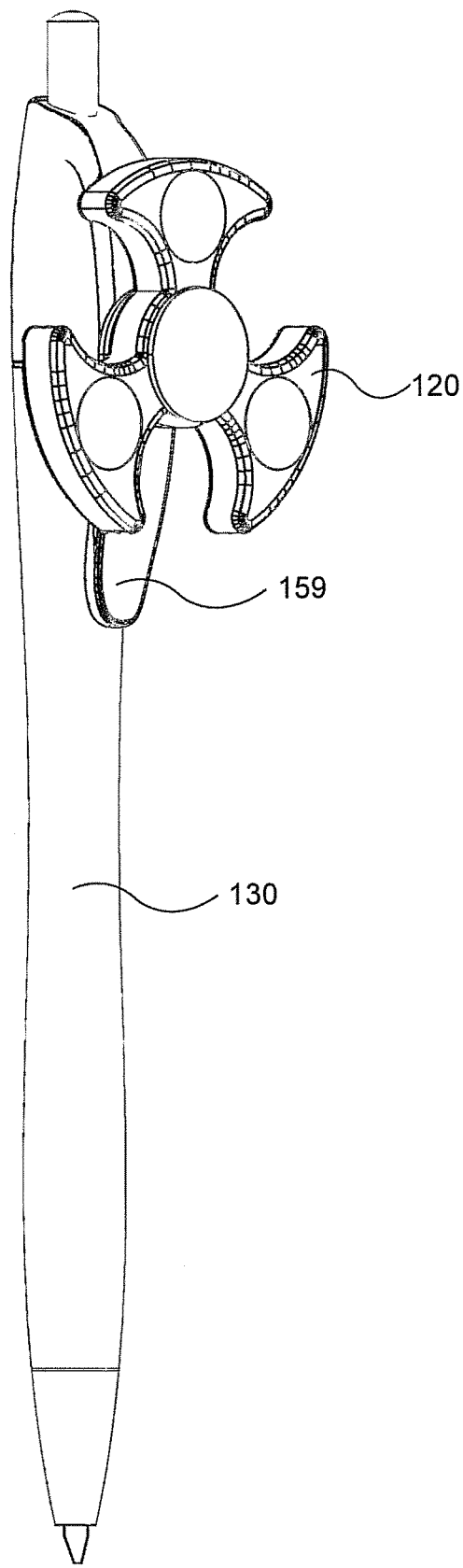
FIG. 13 is a front perspective view of an additional embodiment of the writing instrument with a bearing coupled rotary sensory device in accordance with the invention.

The rotary device 120 may be coupled to the writing instrument 130 at any desired location. For example, as shown in FIGS. 1 and 2A, the rotary device may be affixed to the top portion of the writing instrument via a post or plunger. In other embodiments, the rotary device is inserted over the body of the writing instrument through the central opening and placed at any desired position along the body, such as shown in FIG. 12. In yet other embodiments, the rotary device 120 is coupled to a pen clip 159, as illustrated in FIG. 13. The rotary device and the bearing may be coupled to the pen clip 159 via any suitable mechanism discussed above.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A writing instrument, comprising:
    a barrel with a first end and a second end and a longitudinal axis, wherein the first end is directly coupled to a post and the second end has an aperture for a writing tip to be exposed, wherein the post is a unitary piece and wherein the post actuates the writing tip of the writing instrument;
    a rotary bearing coupled to the post, wherein the rotary bearing has a central opening and wherein the post at least partially extends through the central opening of the rotary bearing; and
    a rotary device coupled to the bearing;
    wherein, once the writing instrument is assembled, the first and second ends of the barrel do not move with respect to each other along the longitudinal axis of the barrel.

2. The writing instrument of claim 1, wherein the rotary device is powered by a non-electric power.

3. The writing instrument of claim 1, wherein the rotary bearing comprises an inner race and an outer race and a plurality of rolling elements positioned between the inner race and the outer race.

4. The writing instrument of claim 1, wherein the rotary device comprises a rotary sensory device.

5. The writing instrument of claim 1, wherein the post comprises a plurality of external threads, wherein the rotary bearing is coupled to the post via a screw cap such that the rotary bearing is positioned between the first end of the writing instrument and the screw cap, and wherein the screw cap includes a plurality of threads inside of the screw cap that interact with the plurality of external threads on the post.

6. The writing instrument of claim 1, further comprising:
    a support member having a base plate with a central opening and a hollow cylindrical body extending from the base plate, wherein the post is extended through the central opening and the hollow cylindrical body of the support member, and
    a cap coupled to the hollow cylindrical body of the support member, wherein the rotary bearing is supported between the base plate and the cap.

7. A writing instrument, comprising:
    an elongated body with a central portion and opposite ends wherein one of said ends of the elongated body has an aperture through which a writing implement is exposed;
    a rotary bearing coupled to said elongated body, wherein said elongated body extends through a central opening of the rotary bearing such that each end of the elongated body extends from the rotary bearing; and
    a rotary device coupled to the bearing, wherein the rotary device is not powered by an electric power.

8. The writing instrument of claim 7, wherein the rotary device is actuated by manually exerting a rotational force on the rotary device.

9. The writing instrument of claim 7, wherein the bearing comprises an inner race and an outer race and a plurality of rolling elements positioned between the inner race and the outer race.

10. The writing instrument of claim 9, wherein the rolling elements are balls.

11. The writing instrument of claim 7, wherein the rotary device comprises a rotary sensory device.

12. The writing instrument of claim 7, wherein the rotary device comprises a plurality of wings.

13. The writing instrument of claim 7, wherein the rotary device comprises an object.

14. The writing instrument of claim 7, wherein the rotary device comprises a wheel.

15. The writing instrument of claim 7, wherein the writing instrument is a pen.

16. The writing instrument of claim 7, wherein the rotary device is not electrically powered.

17. The writing instrument of claim 7, wherein the rotary bearing is coupled to said elongated body via an adhesive.

18. The writing instrument of claim 7, wherein the rotary bearing is coupled to said elongated body via friction between the inner race of the rotary bearing and the elongated body.

19. A writing instrument, comprising:

an elongated body with a first end and a second end, wherein the second end has an aperture for a writing tip to be exposed;

a clip coupled to the elongated body adjacent the first end;

a rotary bearing positioned on the clip; and a rotary device coupled to the bearing;

wherein the rotary bearing comprises an inner race and an outer race and a plurality of rolling elements positioned between the inner race and the outer race.

20. The writing instrument of claim 19, wherein the elongated body has a longitudinal axis extending from the first end to the second end and wherein the rotary device has a plane of rotation, wherein the plain of rotation is substantially parallel to the longitudinal axis of the elongated body.

* * * * *